US012748120B2

(12) United States Patent
Allain

(10) Patent No.: US 12,748,120 B2
(45) Date of Patent: Sep. 29, 2026

(54) HIV VIRAL LOAD TESTING

(71) Applicant: DIAGNOSTICS FOR THE REAL WORLD, LTD, San Jose, CA (US)

(72) Inventor: Jean-Pierre Allain, Cambridgeshire (GB)

(73) Assignee: DIAGNOSTICS FOR THE REAL WORLD, LTD, San Jose, CA (US)

(*) Notice: Subject to any disclaimer, the term of this patent is extended or adjusted under 35 U.S.C. 154(b) by 0 days.

(21) Appl. No.: 16/133,784

(22) Filed: Sep. 18, 2018

(65) Prior Publication Data

US 2019/0018035 A1 Jan. 17, 2019

Related U.S. Application Data

(63) Continuation of application No. 14/776,900, filed as application No. PCT/GB2014/050821 on Mar. 14, 2014, now Pat. No. 10,184,950.

(30) Foreign Application Priority Data

Mar. 15, 2013 (GB) ..................................... 1304797
Oct. 1, 2013 (GB) ..................................... 1317376

(51) Int. Cl.

*C12Q 1/6806* (2018.01)
*C12N 7/02* (2006.01)
*C12Q 1/686* (2018.01)
*C12Q 1/70* (2006.01)
*G01N 35/10* (2006.01)
*B01L 3/00* (2006.01)
*G01N 30/00* (2006.01)
*G01N 30/60* (2006.01)
*G01N 30/88* (2006.01)
*G01N 35/00* (2006.01)
*G01N 35/04* (2006.01)

(52) U.S. Cl.

CPC ........... *G01N 35/1011* (2013.01); *C12N 7/02* (2013.01); *C12Q 1/6806* (2013.01); *C12Q 1/686* (2013.01); *C12Q 1/703* (2013.01); *G01N 35/10* (2013.01); *B01L 3/5635* (2013.01); *B01L 2200/026* (2013.01); *B01L 2200/10* (2013.01); *B01L 2300/0681* (2013.01); *C12N 2740/16011* (2013.01); *C12Q 2545/10* (2013.01); *G01N 2030/009* (2013.01); *G01N 30/6091* (2013.01); *G01N 2030/8827* (2013.01); *G01N 2035/00475* (2013.01); *G01N 2035/0436* (2013.01); *G01N 2035/1053* (2013.01)

(58) Field of Classification Search

CPC ..... C12Q 1/686; C12Q 1/703; B01L 2200/10; B01L 3/5635; B01L 2300/0681; G01N 2035/00475; G01N 2030/009; G01N 2030/8827; G01N 2035/1053; C12N 2740/16011

See application file for complete search history.

(56) References Cited

U.S. PATENT DOCUMENTS

| | | | | |
|---|---|---|---|---|
| 5,108,899 | A | 4/1992 | Allen | |
| 5,200,151 | A | 4/1993 | Long | |
| 5,620,853 | A | 4/1997 | Smethers et al. | |
| 2003/0129741 | A1 | 7/2003 | Ramstad | |
| 2003/0138941 | A1* | 7/2003 | Gong .................... | B01L 3/5027 435/287.2 |
| 2003/0150793 | A1 | 8/2003 | Verpoort et al. | |
| 2004/0071602 | A1 | 4/2004 | Yiu | |
| 2005/0089450 | A1 | 4/2005 | Al-Mahareeq et al. | |
| 2006/0034732 | A1 | 2/2006 | Bargh et al. | |
| 2006/0118491 | A1 | 6/2006 | Gjerde et al. | |
| 2009/0129978 | A1 | 5/2009 | Wilson et al. | |
| 2009/0155123 | A1 | 6/2009 | Williams et al. | |
| 2010/0028204 | A1 | 2/2010 | Lee et al. | |
| 2010/0119416 | A1 | 5/2010 | Tajima | |
| 2010/0143905 | A1* | 6/2010 | Lane ..................... | B01L 3/5023 435/6.16 |
| 2010/0180980 | A1 | 7/2010 | Lee et al. | |
| 2011/0312856 | A1* | 12/2011 | Silverbrook .......... | F16K 99/003 506/40 |
| 2012/0028342 | A1* | 2/2012 | Ismagilov ......... | B01L 3/502738 435/283.1 |
| 2012/0088244 | A1 | 4/2012 | Owen et al. | |
| 2012/0156306 | A1 | 6/2012 | Weissman et al. | |

FOREIGN PATENT DOCUMENTS

| | | | |
|---|---|---|---|
| CN | 202803267 | U | 3/2013 |
| DE | 102004025588 | A1 | 12/2005 |
| EP | 0 114 686 | A2 | 8/1984 |

(Continued)

OTHER PUBLICATIONS

Revets et al. Journal of Clinical Microbiology. 1996. 34(5):1058-1064. (Year: 1996).*
Shibata et al. Masui. 1991. 40(10):1531-5, Abstract. (Year: 1991).*
Richter et al. Leukocyte Depletion of Red Cell Preparations: Fourth Filter Generation Leads To 4LOG Reduction. How Far Can/Should We Go? Immunology and Blood Transfusion. 1993. (Year: 1993).*
Guidance for Industry: Nucleic Acid Testing (NAT) for Human Immunodeficiency Virus Type 1 (HIV-1) and Hepatitis C Virus (HCV): Testing, Product Disposition, and Donor Deferral and Reentry, U.S. Department of Health and Human Services, FDA, May 2010, 47 pages.

(Continued)

*Primary Examiner* — Joseph G. Dauner
(74) *Attorney, Agent, or Firm* — Scully, Scott, Murphy & Presser, P.C.

(57) ABSTRACT

Methods of testing HIV viral load are described. The methods comprise detecting HIV viral RNA in a sample of leukocyte-depleted blood. Such methods can be carried out on low-volume samples obtained without the need for venipuncture or a centrifuge. The methods are particularly suited for HIV viral load testing in resource-limited settings. Methods for monitoring HIV infection are also described, as well as kits for carrying out the methods.

11 Claims, 5 Drawing Sheets

(56) References Cited

FOREIGN PATENT DOCUMENTS

| | | | | |
|---|---|---|---|---|
| EP | 0 701 865 | A1 | 3/1996 | |
| EP | 2 453 219 | A1 | 5/2012 | |
| FR | 2 220 135 | A7 | 9/1974 | |
| FR | 2 969 128 | A1 | 6/2012 | |
| GB | 1 463 807 | | 2/1977 | |
| GB | 2 443 243 | A | 4/2008 | |
| JP | 2011-17568 | A | 1/2011 | |
| WO | WO-9316201 | A1 * | 8/1993 | ......... B01D 17/0217 |
| WO | WO 99/46046 | A1 | 9/1999 | |
| WO | WO 01/56695 | A1 | 8/2001 | |
| WO | WO 02/48164 | A2 | 6/2002 | |
| WO | 2004/026372 | A1 | 4/2004 | |
| WO | 2007/025738 | A1 | 3/2007 | |
| WO | WO 2008/012550 | A2 | 1/2008 | |
| WO | 2008/090340 | A2 | 7/2008 | |
| WO | WO 2009/121034 | A2 | 10/2009 | |
| WO | WO 2010/015835 | A1 | 2/2010 | |
| WO | WO 2010/075116 | A2 | 7/2010 | |
| WO | WO 2011/012859 | A1 | 2/2011 | |
| WO | WO 2012/017238 | A1 | 2/2012 | |
| WO | WO 2012/040333 | A1 | 3/2012 | |
| WO | WO 2012/134440 | A1 | 10/2012 | |
| WO | WO 2013/016629 | A1 | 1/2013 | |

OTHER PUBLICATIONS

Hess, C. et al., "Association of a pool of HIV-1 with erythrocytes in vivo: a cohort study", The Lancet (2002), vol. 359, pp. 2230-2234.
Alp, A. et al., "Comparison of 3 nucleic acid isolation methods for the quantification of HIV-1 RNA by Cobas Taqman real-time polymerase chain reaction system", Diagnostic Microbiology and Infectious Disease (2009), vol. 63, pp. 365-371.
Beck, Z. et al., "Human Erythrocytes Selectively Bind and Enrich Infectious HIV-1 Virions", PLoS ONE, (Dec. 2009), vol. 4, Issue 12, pp. 1-8.
Boom, R. et al., "Rapid and Simple Method for Purification of Nucleic Acids", Journal of Clinical Microbiology, (Mar. 1990), vol. 28, No. 3, pp. 495-503.
Candotti, D. et al., "Multiplex real-time quantitative RT-PCR assay for hepatitis B virus, hepatitis C virus, and human Immunodeficiency virus type 1", Journal of Virological Methods, (2004), vol. 188, pp. 39-47.
"illustra plasmidPrep Mini Spin Kit", GE Healthcare, Plasmid DNA puricication, (Jan. 2007), 5 pages.
Hourfar, M.K. et al., "High-Throughput Purification of Viral RNA Based on Novel Aqueous Chemistry for Nucleic Acid Isolation", Clinical Chemistry, (2005), vol. 51, No. 7, pp. 1217-1222.
"AIDSinfo: Guidelines for the Use of Antiretroviral Agents in HIV-1-Infected Adults and Adolescents", Downloaded from http://aidsinfo.nih.gov/guidelines on Sep. 24, 2013, 267 pages.
Novotny, V.M. et al., "Occurrence of Allogeniec HLA and Non-HLA Antibodies After Transfusion of Prestorage Filtered Platelets and Red Blood Cells: A Prospective Study", Blood, (Apr. 1, 1995), vol. 85, No. 7, pp. 1736-1741.
"COBAS TaqMan HIV-1 Test, v2.0 For Use With The High Pure System", http:/molecular.roche.com/assays/Pages/COBASTaqManHIV-1Testv2.0ForUseWith . . . , printed on Jul. 25, 2013, 3 pages.
Sharma, R.R et al., "Leukoreduced blood components: Advantages and strategies for its implementation in developing countries", Asian J.Transfus Sci, (Jan. 2010), vol. 4, No. 1, 12 pages.
Wan, H. et al., "Coamplification of HIV-1 Proviral DNA and Viral RNA in Assays Used for Quantification of HIV-1 RNA", Journal of Clinical Microbiology, (Jun. 2010), vol. 48, No. 6, pp. 2186-2190.
International Search Report dated Jul. 25, 2014 issued in PCT/GB2014/050820.
European Search Report dated Feb. 21, 2014 issued in EP 13 18 8269.
Search Report dated Mar. 14, 2014 issued in GB 1304797.2.
Search Report dated Sep. 2, 2013 issued in GB 1304797.2.
Stevens, W. S., et al., "Quantifying HIV for Monitoring Antiretroviral Therapy in Resource-Poor Settings" The Journal of Infectious Diseases (2010), vol. 201, pp. S16-S26.
Al-Muharrmi, Z., et al. "HIV-1 Viral Load After Leukodepletion" Lippincott Williams & Wilkins 48(2):224-225 2008.
Ariga. H., et al., "Residual WBC subsets in filtered prestorage RBCs" Transfusion 43:98-106 (2003).
Bertagnolio, S., et al., "Dried blood spots for HIV-1 Drug Resistance and Viral Load Testing: A Review of Current Knowledge and WHO Efforts for Global HIV Drug Resistance Surveillance" AIDS Rev. 12:195-208 (2010).
International Search Report (citations page) issued in International Application No. PCT/GB2014/050821 dated Jul. 2, 2014.
Lee, H. H., et al. "Simple Amplification-Based ASsay: A Nucleic Acid-Based Point-of-Care Platform for HIV-1 Testing" JID 201 (Suppl 1):565-572 (2010).
Paunovic, D., et al., "Multicenter evaluation of a whole-blood filter that saves platelets." Transfusion 44(8):1192-203 (2004) Abstract only.
Pilcher, C. D., et al., "Public Health Rationale for Rapid Nucleic Acid or p24 Antigen Tests for HIV" JID 201 (Suppl 1):S7-S15 (2010).
Puren, A., et al., "Laboratory Operations, Specimen Processing, and Handling for Viral Load Testing and Surveillance" JID 201 (Suppl 1):S27-S36 (2010).
Rawal, J. D., et al., "Reduction of human immunodeficiency virus-infected cells from donor blood by leukocyte filtration" Transfusion 29(5):460-462 (1989).
Rawal B. D., et al., "Evaluation of Leukocyte Removal Filters Modelled by Use of HIV-Infected Cells and DNA Amplification" Blood 76(10):2159-2161 (1990).
Schito, M. L., et al., "Challenges for Rapid Molecular HIV Diagnostics" JID 201 (Suppl 1):S1-S6 (2010).
Snyder, El., et al., "In vitro and in vivo evaluation of a whole blood platelet-sparing leukoreduction filtration system" Transfusion 50(10:2415-51 (2010) Abstract only.
Stevens, W. S., et al., "Challenges in Implementing HIV Load Testing in South Africa" JID 201 (Suppl 1):S78-S84 (2010).
Tanriverdi, S., et al., :A Rapid and Automated Sample-to Result HIV Load Test for Near-Patient Application JID 201 (Suppl 1) S52-S58 (2010).
United Kingdom Search Report (citations page) issued in Application No. GB1317376.0 dated Mar. 4, 2014.
Usdin, M., et al., "Patient Needs and Point-of-Care Requirements for HIV Load Testing in Resource-Limited Settings" JID 201 (Suppl 1):S73-S77 (2010).
Weinauer, F., et al., "Supply with Platelet Concentrates from the Point of View of a Blood Donation Service of the Bavarian Red Cross" Transfus Med Hemother 35:114-116 (2008).
World Health Organization, "Consolidated Guidelines on the Use of Antiretroviral Drugs for Treating and Preventing HIV Infection" 272 pages (2013).

* cited by examiner

HIV VIRAL LOAD TESTING

CROSS REFERENCE TO RELATED APPLICATIONS

This application claims the benefit of priority from U.S. patent application Ser. No. 14/776,900, filed Sep. 15, 2015; which is a national stage entry of the PCT Application No: PCT/GB2014/050821 filed Mar. 14, 2014; which claims priority to GB Patent Application No: 1317376.0 filed Oct. 1, 2013 and GB Patent Application No: 1304797.2, the entire contents of which are incorporated herein by reference.

This invention relates to testing of HIV viral load (VL), to kits for carrying out such tests, and to methods for monitoring HIV infection.

Viral load is a measure of the severity of a viral infection. Viral load can be used to monitor viral infection, guide treatment, determine the effectiveness of treatment, and predict how a disease caused by the infection may progress. Measurement of viral load is of particular importance for the treatment of HIV infection.

In conventional methods for determining HIV viral load, a whole blood sample is obtained from a patient by venipuncture. Cells are then removed from the sample by centrifugation to provide plasma, and the number of copies of HIV RNA per millilitre of plasma is determined, for example, by reverse-transcriptase polymerase chain reaction (RT-PCR), branched DNA (bDNA), or nucleic acid sequence-based amplification (NASBA) analysis. If a subject has a high HIV viral load (for example, at least 1,000 copies/ml plasma), this may indicate treatment failure, i.e. that the virus is replicating and the disease may progress more quickly. If HIV viral load is low (for example, less than 1,000 copies/ml plasma), this indicates that the anti-viral treatment regimen is effective, i.e. that the virus may not be actively replicating and the disease may progress more slowly.

HIV VL testing traditionally employs plasma as the sample medium because plasma is devoid of CD4+ cells that carry proviral DNA and platelets (which carry surface-bound HIV). A further advantage of using plasma is that it lacks red blood cells. Haemoglobin in these cells can inhibit amplification reactions used to determine the number of copies of HIV RNA. However, the disadvantages of using plasma include the requirement for a trained phlebotomist and centrifugal equipment. Neither of these may be available, particularly where it is desired to carry out the test in resource-limited settings, such as at a remote location or in a physician's office. There is also some evidence that plasma is not totally devoid of proviral DNA, possibly because of cell disruption during handling of the blood sample (Wan et al 2010. J Clin. Microbiol., 48, 2186-90).

There is a need, therefore, to provide HIV viral load tests that can be carried out without the need for venipuncture and centrifuge equipment.

The Applicant has appreciated that these disadvantages of using plasma may be overcome by using leukocyte depleted blood for HIV viral load testing. Leukocyte depleted blood is depleted of CD4+ cells (including monocytes) which may contain HIV DNA, and so may be used directly to detect HIV RNA as a measurement of HIV viral load.

The Applicant has also appreciated that sufficient blood for leukocyte depletion can be obtained from a simple heel or finger prick, and that leukocyte depletion can be carried out without a centrifuge.

According to the invention there is provided a method of testing (i.e. determining) HIV viral load, which comprises detecting HIV viral RNA in a sample of leukocyte depleted blood.

The term "leukocyte-depleted blood" is used herein to refer to whole blood that has been selectively depleted of leukocytes ("leukodepleted"). Preferably the sample of leukocyte-depleted blood has been depleted of at least 99.9% (i.e. equal to or greater than 3 log reduction) of the leukocytes present in a whole blood sample from which the leukocyte-depleted sample was obtained. Preferably the leukocyte-depleted blood retains at least some, preferably a minimum of 50%, 60%, 70%, or 80%, more preferably a minimum of 85%, 90% or 95%, of the red blood cells present in the whole blood sample from which the leukocyte-depleted sample was obtained. The leukocyte-depleted blood may also retain some of the platelets present in the whole blood sample from which the leukocyte-depleted sample was obtained, for example, at least 50%, 60%, 70%, 80%, or 85% of the platelets. For example, the leukocyte-depleted blood may retain a minimum of 85% of the red blood cells, and at least 50% of the platelets present in the whole blood sample from which the leukocyte-depleted sample was obtained. The leukocyte-depleted blood may retain a minimum of 85% of the red blood cells, and at least 85% of the platelets present in the whole blood sample from which the leukocyte-depleted sample was obtained.

A sample of leukocyte-depleted blood is distinguished herein from a sample of plasma. Plasma samples lack blood cells, and are prepared, for example, by spinning a tube of fresh blood containing an anticoagulant in a centrifuge until the blood cells fall to the bottom of the tube.

A sample of leukocyte-depleted blood may be prepared by depleting a whole blood sample of leukocytes. Leukocyte depleted blood can readily be prepared by filtering whole blood through a leukoreduction filter. Other suitable methods include centrifugation and buffy coat removal, and blood component collection through apheresis technology (Novotny et al., Blood. 1995; 85:1736-41). Leukodepletion using leukoreduction filters or apheresis devices readily achieves greater than 3 log leukodepletion. Use of leukoreduction filters is particularly preferred because no specialist equipment is required, and they can be used with low-volume samples, making them particularly suitable for use in resource-limited settings.

The term "leukoreduction filter" is used herein to mean a material that is able to filter and selectively remove white blood cells from whole blood to produce leukodepleted blood. Current leukoreduction filters include depth filters and screen filters. Depth filters comprise non-woven filter material in the form of compressed wool fibres arranged in an irregular fashion, or non woven synthetic material, for example molten polymers that are blown into fine fibres to form an irregular web of material with a high internal surface area. Screen filters comprise woven filter material in the form of fibres arranged in multiple layers in a regular fashion. The filters allow red blood cells, plasma and, to some extent, platelets to pass through.

Preferred leukoreduction filters comprise polybutylene terephthalate (PBT), polypropylene (PP), polyvinylidene difluoride (PVDF), or a mixture of these materials. Preferred pore sizes range from 0.5-20 μm. Suitable leukoreduction filters are described in US 2003/0150793. Particularly preferred filter materials are described in the Materials and Methods section of the Examples below.

The primary mechanism of leukocyte removal by leukoreduction filters is by trapping the leukocytes in small pores, while allowing other blood components to pass through. When observed under a scanning electron microscope, leukocytes in the filter are not seen to deform, even when trapped in filter pores, which taper to a narrower diameter than the cell itself. In contrast, red blood cells are deformable and are able to pass through the filter. When fixed with glutaraldehyde, red blood cells can be captured in the filter matrix (Kora 1993. Mechanism of leukocyte removal by porous material IN: Hokkaido Symposium on Tranfusion Medicine, $3^{rd}$ ed., Blackwell Science Inc.). Platelets can pass through the pores in the filter by virtue of their smaller size. Leukocytes are also removed by adsorption to the filter material. Adsorption can be increased by surface modifying the filter. For example, coating the filter material with methacrylate polymers creates a stronger positive charge for adsorption of the negatively charged leukocytes, and increases the efficiency of the filter (Sharma and Marwaha, Asian J. Transfus. Sci., 2010, January; 4(1): 3-8).

Filters currently in production include LEUCOFLEX MTLI (Macopharma), LEUCOFLEX LXT (Macopharma), COMPOSELECT WB (Fresenius), SEPACELL RZ-2000F (Asahi KASEI), IMMUFLEX WB-SP (Terumo) and LEUKOTRAP WBF3 (Haemonetics). All of these filters remove leukocytes and (at least some) platelets from whole blood. The amount of red blood cells retained is ~6%. This leaves ~94% erythrocytes in the leukodepleted sample. These filters remove leukocytes to the level accepted for transfusion (a leukocyte content of less than $5\times10^6$ cells/unit, which equates to a greater than 3 log, or greater than 99.9%, reduction).

The percentage of leukocytes remaining in the leukodepleted blood may be determined, for example, by counting the number of leukocytes before and after leukodepletion by flow cytometric analysis, or by determining the number of CD45 positive cells, using reverse transcription (RT) and real-time polymerase chain reaction (qPCR) quantification of CD45 mRNA before and after leukodepletion, as described in the Materials and Methods section of the Examples below.

Preferably the whole blood sample is an anticoagulated whole blood sample. A preferred anticoagulant is ethylenediaminetetraacetic acid (EDTA), particularly dipotassium EDTA ($K_2$EDTA). Viral particles have been shown to adhere to the surface of red blood cells, but not in the presence of EDTA (Beck et al. 2009. Human erythrocytes selectively bind and enrich infectious HIV-1 virions. PLoS One, 4, e8297). Consequently, viral load test results from plasma and leukodepleted blood samples should be comparable when prepared from EDTA-treated whole blood. Crystallised anticoagulants are preferred, since liquid anticoagulants dilute the sample.

It is particularly preferred that the whole blood sample used for leukodepletion is a low volume whole blood sample (preferably up to 500 µl, for example 100-500 µl, or up to 300 µl, for example 100-300 µl), since such samples can be obtained without venipuncture.

Preferably the whole blood sample is, or has been, obtained from a subject by finger prick or heel prick, for example using a lancet. Such methods typically provide whole blood samples up to ~500 µl.

A blood collector may be used to collect the whole blood sample. Suitable low-volume blood collectors include capillary tubes and microtainers. A suitable blood collector is a RAM Scientific "SAFE-T-FILL" Capillary Blood Collection Tube. The collection tube is pre-assembled with a capillary tube, attached cap and a micro tube. The capillary tube is coated with anticoagulant. The microtubes come in a variety of sizes, to allow collection of 150, 200, or 300 µl samples. Suitable microtainers include microtainer blood collection tubes of Becton, Dickinson and Company.

A sample of whole blood may be collected, for example, from a finger prick, and then processed by passing the sample through a leukoreduction filter. If the sample volume is small (typically ~150 µl from a finger prick), it may be necessary to dilute the sample with an isotonic solution, or to wash the filter with isotonic solution.

Thus, the whole blood sample used for leukodepletion may be a diluted whole blood sample. Methods of the invention may further comprise diluting the whole blood sample prior to leukodepletion. Dilution of the whole blood sample 1-in-2, or 1-in-3, for example with an isotonic solution, such as phosphate buffered saline (PBS), is preferred.

Conventional leukoreduction filters are dependent on gravity alone to cause blood to pass through the filter. However, it may be necessary to apply a pressure differential across the filter to cause the sample to pass through the filter, for example for small sample sizes.

For low volume samples in particular, it may be necessary to optimise the filtration conditions, for example the type of filter, the thickness of filter, the volume of sample, and the flow rate of sample through the filter, to maximise the number of leukocytes removed by the leukoreduction filter, whilst minimising the dead volume (i.e. the amount of sample that remains associated with the filter after filtration) of the filter. We have found that for a whole blood sample of 100 µl, diluted with 200 µl phosphate buffered saline (PBS), excellent leukodepletion (i.e. greater than 3 log reduction), and low filter dead volume, is achieved using eight layers of Macopharma filter at a pump flow rate of 50 µl air per second.

The sample of leukocyte-depleted blood may be a stored sample. For example, a whole blood sample obtained from a subject may be leukodepleted, and then stored in liquid, frozen, or dry form prior to detecting HIV viral RNA in the sample. Storage of the sample will be required when detection of HIV viral RNA in the sample is carried out at a different location to leukodepletion. Storage of the leukodepleted sample in dried form is preferred since this minimises the cost and inconvenience of storage and transport of the sample.

If the sample has been stored in dry form, it will generally require rehydration prior to detecting HIV viral RNA. Thus, the sample of leukocyte depleted blood may be a rehydrated dried sample of leukocyte depleted blood. Methods of the invention may further comprise drying the sample of leukocyte depleted blood, and rehydrating the sample prior to detection of HIV viral RNA.

It will be appreciated that methods of the invention are carried out without preparing a plasma sample.

Preferably HIV viral RNA present in a sample of leukocyte depleted blood is detected by extracting nucleic acid from the sample and detecting HIV viral RNA present in the extracted nucleic acid.

Many suitable methods for extraction (i.e. isolation) of nucleic acid are known to the skilled person. Some methods use chaotropic agents, such as guanidinium thiocyanate, and organic solvents to lyse cells, and denature proteins. For example, Boom et al. (Journal of Clinical Microbiology, 1990, Vol. 28(3): 495-503) describes methods in which a sample is contacted with silica particles in the presence of a lysis/binding buffer containing guanidinium thiocyanate. Released nucleic acid binds to the silica particles, which are then washed with a wash buffer containing guanidinium thiocyanate, then with ethanol, and then acetone. The bound nucleic acid is subsequently eluted in an aqueous low salt buffer (Tris-HCl, EDTA, pH 8.0).

Preferred methods avoid the requirement for chaotropic salts and organic solvents. For example, Hourfar et al. (Clinical Chemistry, 2005, 51(7): 1217-1222) describes methods in which a sample is mixed with magnetic silica particles in the presence of a lysis/binding buffer containing a kosmotropic salt (ammonium sulphate) before addition of proteinase K. Following separation, the magnetic particles are washed with wash buffer containing proteinase K, and eluted in elution buffer (Tris-HCl, pH 8.5) at 80° C. Other preferred methods are described in WO 2010/015835.

Isolation of nucleic acid may be carried out using conventional binding buffers and/or elution buffers for use with a solid phase that is able to bind the nucleic acid in the presence of binding buffer at a first pH, and from which the nucleic acid can be eluted at a second pH.

The solid phase preferably comprises an ionisable group, which changes charge according to the ambient conditions. The pKa of the ionisable group is appropriate to the conditions at which it is desired to bind nucleic acid to and release nucleic acid from the solid phase. Generally, nucleic acid will bind to the solid phase at a pH below or roughly equal to the pKa, and will be released at a higher pH (usually above the pKa). Suitable solid phases for binding a nucleic acid at a first pH, and elution of bound nucleic acid at a second pH that is higher than the first pH, are well known to those of ordinary skill in the art. For example, at the first pH the solid phase may comprise a positive charge, and at the second pH the solid phase may have a less positive, neutral, or negative charge. Alternatively or additionally, at the first pH the solid phase may comprise a neutral or less negative charge, and at the second pH the solid phase may have a negative or more negative charge. Such changes in charge allow the nucleic acid to be adsorbed to the solid phase at the first pH, and released at the second pH.

For example, the solid phase may comprise a negatively ionisable group with a pKa between the first and second pH. Nucleic acid will bind to the solid phase when the solid phase is neutral or less negatively charged, and will be released when the solid phase is negatively or more negatively charged. Alternatively, or additionally, the solid phase may comprise a positively ionisable group with a pKa between the first and second pH. Nucleic acid will bind to the solid phase when the solid phase is positively charged, and will be released when the solid phase is neutral or less positively charged.

Examples of solid phases that may be used for extraction of nucleic acid include solid phases that comprise inorganic oxides, such as silica or glass (for example, as described in Boom et al, or Hourfar et al), or aluminium oxide, sugar polymers, or charge-switch materials (for example, as described in WO 02/48164).

The solid phase may be in any suitable form, for example comprising a membrane, gel, or particles, for example magnetic particles. Silica membrane or gel, and magnetic silica particles are preferred examples. Silica membrane is particularly preferred. This is less expensive than magnetic silica particles (used for example by Hourfar, et al.) and does not require refrigerated storage, unlike magnetic silica particles.

Preferably the solid phase is a solid phase to which binding of nucleic acid is enhanced by the presence of a kosmotropic agent. Preferably binding of the nucleic acid to the solid phase is carried out in the presence of a kosmotropic agent. Such agents are known to enhance binding of nucleic acid to solid phases such as silica-based solid phases.

The terms "chaotropic" and "kosmotropic" agent originate from the Hofmeister series (Cacace et al., Q Rev Biophys 1997; 30:241-77), which divides these agents depending on their influence on the structure of macromolecules and water. A chaotrope may be defined as a substance that breaks solvent structure, and a kosmotrope as a substance that enhances solvent structure. FIG. 1 of Cacace et al shows the Hofmeister series and commonly occurring organic solutes with effects on protein structure/function. Examples of chaotropic agents are known to those in the art, and include sodium iodide, sodium perchlorate, guanidinium thiocyanate and guanidinium hydrochloride. Examples of kosmotropic agents are known to those in the art, and include ammonium sulphate and lithium chloride.

Lysis is preferably carried out using the binding buffer. Binding buffers that may be used for cell lysis are known to those of ordinary skill in the art. The lysis buffer used by Boom et al. comprises guanidinium thiocyanate, Tris hydrochloride, pH 6.4, EDTA (adjusted to pH 8), and Triton X-100. However, it is preferred that the lysis buffer does not include a chaotropic agent. Preferred lysis/binding buffers for use according to the invention comprise a kosmotropic agent. Preferably the buffer is an acidic buffer, suitably a strong acidic buffer with a pKa (25° C.) in the range 3-5.

HIV viral RNA may be detected using any suitable method. A variety of suitable methods are known to the skilled person, including RT-PCR, bDNA, or NASBA analysis. Preferably HIV viral RNA is detected by amplifying the HIV viral RNA, and detecting the amplified HIV viral RNA. Signal amplification methods, such as branched DNA (bDNA) assays can also be used.

Preferred methods of HIV viral RNA detection are methods that can readily be used in resource-limited settings. Preferred examples of such methods comprise isothermal nucleic acid amplification of reverse transcribed HIV viral RNA, since such methods do not require the use of thermal cyclers which may not be available in resource-limited settings. Examples of particularly preferred methods are described in WO 2008/090340 and Lee et al., Journal of Infectious Diseases 2010; 201(S1):S65-S71.

A product of the isothermal nucleic acid amplification may be labelled with a visually detectable label (i.e. a label that is visually detectable without the use of instrumentation), and captured and detected using a chromatographic test strip, for example as described in WO 2008/090340, and Lee et al., Journal of Infectious Diseases 2010; 201(S1): S65-S71.

Methods of the invention may comprise determining whether the viral load is above or below a pre-determined cut-off value for virologic failure. Such methods do not require that a determination of the number of copies of HIV viral RNA/ml is made, only a determination of whether the number of copies is above or below the cut-off value. Such methods are particularly preferred for use in resource-limited settings. Examples of suitable methods are described in Examples 7 and 8 below.

The current World Health Organisation (WHO) virological criterion for treatment failure is 1000 copies per ml or more. In non-resource-limited settings, virologic failure is defined as a viral load above 200 copies/ml (The AIDS Clinical Trials Group, ACTG).

According to some preferred embodiments of the invention, the number of copies of HIV viral RNA/ml of the sample is determined. For example, HIV viral RNA may be detected by reverse transcription of the HIV viral RNA, and subsequent real-time nucleic acid amplification of a product of the reverse transcription. Such methods can be used to provide a quantitative determination of the number of copies of HIV viral RNA/ml of the sample. Such methods may be more suited to use in non-resource-limited settings.

Preferably the HIV viral RNA is HIV-1 viral RNA.

There is also provided according to the invention a method for monitoring HIV infection in a subject, which comprises determining HIV viral load of a sample of leukocyte-depleted blood obtained from the subject, for example using a method of the invention.

Appropriate antiretroviral (ARV) therapy may be administered to the subject depending on the result of the viral load determination. Subjects not infected with HIV, and subjects infected with HIV who are on an effective treatment regime, should have no detectable HIV viral load.

HIV-1 viral load should be measured in all HIV-1-infected patients at baseline (an initial reference value—usually measured when a subject first tests HIV-positive, or starts antiretroviral treatment) and on a regular basis thereafter, especially in patients who are on treatment, because viral load is the most important indicator of response to ARV therapy. Viral load testing serves as a surrogate marker for treatment response and can be useful in predicting clinical progression.

Virologic failure occurs when antiretroviral therapy (ART) fails to suppress and sustain a subject's viral load at a low level. Factors that can contribute to virologic failure include drug resistance, drug toxicity, and poor treatment adherence.

In resource-limited settings, virologic failure is defined as a viral load at or above 1000 copies/ml. Patients diagnosed with HIV infection, but not yet receiving treatment, are administered first-line ART if their viral load is high (for example, 1000 copies/ml or above). Patients already receiving ART should have their viral load monitored to ensure that this treatment is effective (for example, below 1000 copies/ml). If the VL is above 1000 copies/ml, this indicates virologic failure, and it may be necessary to change to a different ART (for example, either an alternative first-line ART, or a second-line ART).

The World Health Organisation (WHO) Consolidated Guidelines on The Use of Antiretroviral Drugs For Treating and Preventing HIV Infection, published June 2013, include recommendations for first-line ART for adults, pregnant and breastfeeding women and their infants, and children, and for second-line ART for adults and adolescents (including pregnant and breastfeeding women), and children (including adolescents).

For adults, the recommended first-line ART is two nucleoside reverse-transcriptase inhibitors (NRTIs) plus a non-nucleoside reverse-transcriptase inhibitor (NNRTI). Tenofovir disoproxil fumarate (TDF) and lamivudine (3TC) (or emtricitabine (FTC)) and efavirenz (EFV) as a fixed-dose combination is recommended as the preferred option to initiate ART. If TDF+3TC (or FTC)+EFV is contraindicated or not available, one of the following options is recommended: zidovudine (AZT)+3TC+EFV; AZT+3TC+nevirapine (NVP); TDF+3TC (or FTC)+NVP. It is recommended that use of stavudine (d4T) in first-line regimens is discontinued.

For adults, the recommended second-line ART is two nucleoside reverse-transcriptase inhibitors (NRTIs) and a ritonavir-boosted protease inhibitor (PI). The following sequence of second-line NRTI options is recommended: after failure on a TDF+3TC (or FTC)-based first-line regimen, use AZT+3TC as the NRTI backbone in second-line regimens; after failure on an AZT or d4T+3TC-based first-line regimen, use TDF+3TC (or FTC) as the NRTI backbone in second-line regimens. Use of NRTI backbones as a fixed-dose combination is recommended as the preferred approach. Heat-stable fixed-dose combinations atazanavir/ritonavir (ATV/r) and lopinavir/ritonavir (LPV/r) are the preferred boosted PI options for second-line ART.

In non-resource-limited settings, virologic failure is defined as a viral load above 200 copies/ml (The AIDS Clinical Trials Group, ACTG). Guidelines for administration of ARV treatment are published by the NIH: "Guidelines for the use of antiretroviral agents in HIV-1-infected adults and adolescents, Department of Health and Human Services, USA".

Thus, according to the invention, for a subject infected with HIV who has not been administered antiretroviral therapy (ART), the subject may be administered ART if the determination of HIV viral load is at or above a pre-determined cut-off value. Preferably the subject is administered a suitable first-line ART.

For a subject infected with HIV who has been administered ART, the subject may be administered a different ART if the determination of HIV viral load is at or above a pre-determined cut-off value for virologic failure. Preferably the subject is administered a suitable second-line ART.

A suitable first- and second-line ART will depend on the age of the subject (and whether they are pregnant or breastfeeding), but can be readily determined by referring to the WHO or NIH Guidelines cited above.

Preferably the cut-off value is 200 copies/ml (suitably for non-resource-limited settings), or 1000 copies/ml (for resource-limited settings).

According to the invention, there is also provided use of leukocyte-depleted blood for HIV viral load testing.

There is further provided according to the invention a kit for HIV viral load testing, which comprises a leukoreduction filter, and a means for detecting HIV viral RNA.

The means for detecting HIV viral RNA preferably comprises reagents required for reverse transcription of HIV viral RNA, and subsequent amplification of a product of the reverse transcription, preferably by isothermal nucleic acid amplification. Suitable reagents are well-known to the skilled person. Examples of suitable reagents are given in WO 2008/090340, and include, for example, a reverse transcriptase, and the following enzyme activities: an RNA-dependent DNA polymerase, a DNA-dependent DNA polymerase, a DNA/RNA duplex-specific ribonuclease, and a DNA-dependent RNA polymerase.

Such kits may further comprise a visually detectable label for labelling a product of the isothermal nucleic acid amplification and/or a chromatographic test strip and reagents for capturing and detecting a product of the isothermal nucleic acid amplification. Suitable labels, test strips, and reagents, and methods for capturing and detecting a product of the isothermal nucleic acid amplification by a simple amplification-based assay (SAMBA), are described in WO 2008/090340 and Lee et al., Journal of Infectious Diseases 2010; 201(S1):S65-S71.

In other embodiments of the invention, the means for detecting HIV viral RNA may comprise reagents required for reverse transcription of HIV viral RNA, and subsequent amplification of a product of the reverse transcription by real-time nucleic acid amplification of the product, preferably for real-time isothermal nucleic acid amplification. Suitable reagents are well-known to the skilled person.

A kit of the invention may further comprise any of the following additional components: a means for applying a pressure differential across the leukoreduction filter; an isotonic solution for diluting a sample of whole blood prior to leukodepletion of the sample; a lancet for obtaining a sample of whole blood from a subject by finger prick or heel prick; a blood collector for collecting a sample of blood from a subject; positive and/or negative controls for use in the HIV viral load test; instructions for carrying out HIV viral load testing using the kit.

A kit of the invention may further comprise means for extracting (i.e. isolating) nucleic acid from a sample of leukocyte depleted blood, for example using a method of nucleic acid extraction as described above. Suitable means for extracting nucleic acid may include a lysis buffer for lysing cells present in the sample, a solid phase for binding nucleic acid, optionally a wash buffer for washing nucleic acid bound to the solid phase, and an elution buffer for eluting nucleic acid from the solid phase. Suitable lysis, wash, and elution buffers are described above, as well as suitable solid phases for use with the buffers.

Embodiments of the invention are described in the following examples with reference to the accompanying drawings in which.

Figure 8:
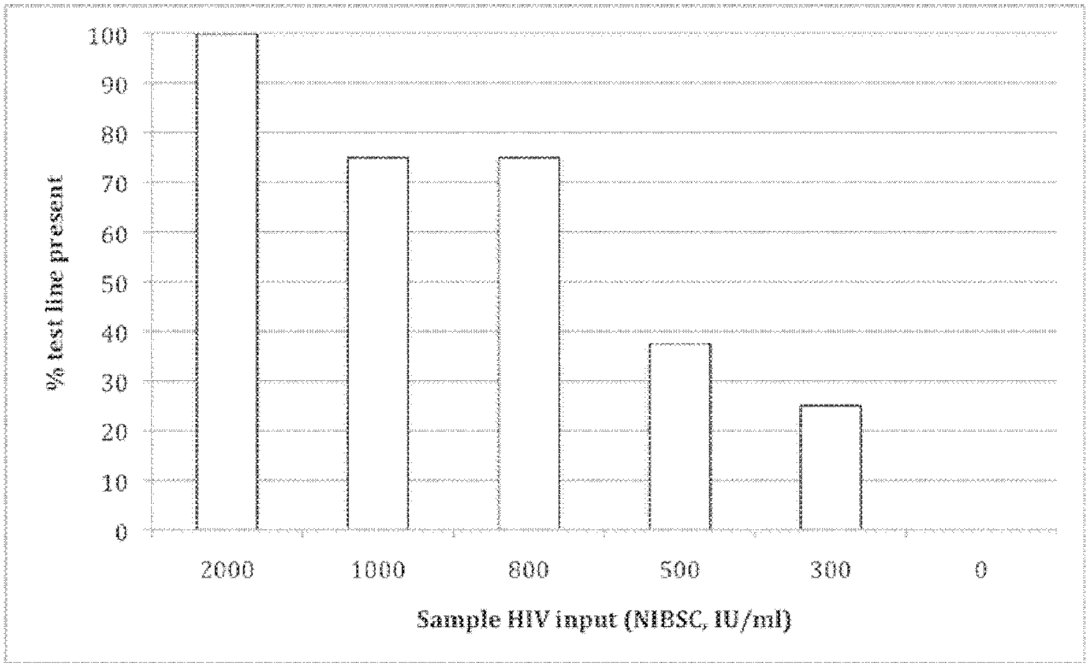
Figure 9:
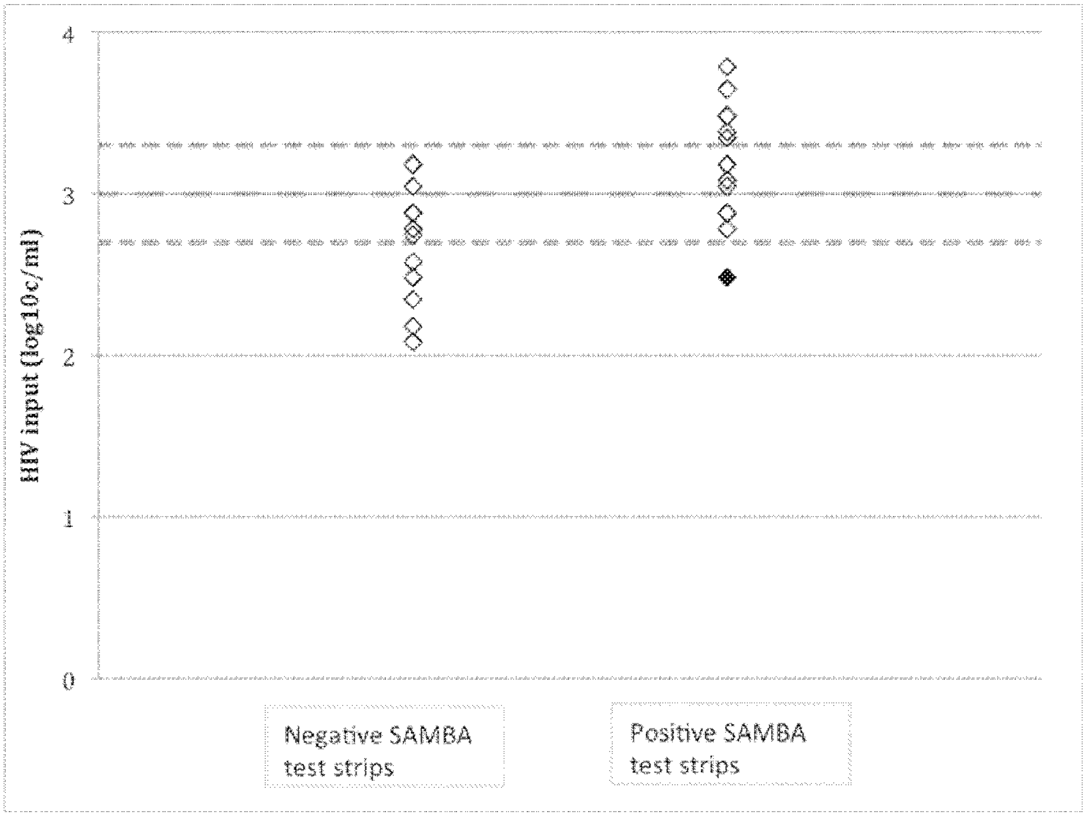

FIG. 8 shows the percentage of test strips with a test line present at a range of input HIV concentrations. In all cases, n=8; and FIG. 9 shows whether positive or negative results were obtained on test strips for a range of input HIV concentrations. Filled markers represent data points which fall outside of the accepted range of 3±0.3 $\log_{10}$ copies/ml.

EXAMPLES

Materials and Methods

Whole blood was spiked with cells of the 8E5 cell line containing one copy of proviral HIV DNA, or with culture supernatant of HIV-1 LAI (RNA, subtype B).

The efficacy of whole blood filtration for nucleated cells was assessed in three different ways:

i) White cell count pre- and post-filtration using a sensitive flow cytometric assay. This method counts white cells present in the whole blood as well as the spiked 8E5 cells;

ii) Relative CD45+ cell amounts were assessed using the Taqman Gene Expression PCR assay (Life Technologies, primer/probe set Hs04189704_m1). The reverse transcription (RT) step required for this assay was completed using the SuperScript III First Strand Synthesis System (Invitrogen) according to the manufacturer's specifications. The CD45 PCR was completed using the Stratagene Mx3000 instrument. This method detects white cells present in the whole blood as well as the spiked 8E5 cells;

iii) Quantification of proviral DNA against a plasmid-derived standard. This was performed by real-time PCR (qPCR) using the Stratagene Mx3000 as previously reported (Candotti et al., J Virol Methods 2004; 118: 39-47: Multiplex real-time quantitative RT-PCR assay for hepatitis B virus, hepatitis C virus and human immunodeficiency virus type 1); HIV-1 RNA was quantified using real-time RT-PCR as previously described (Candotti et al. 2004). The reference used was a secondary standard calibrated using the Artus HIVirus-1 RG RT-PCR kit in copies/ml.

All nucleic acid extractions for PCR and RT-PCR reactions were performed with the High Pure Viral Nucleic Acid kit (Roche), according to the manufacturer's instructions.

Where filtered samples were tested alongside plasma as a comparison to the leukoreduction levels normally employed for viral load testing, plasma was generated by centrifugation at 4,000 rcf (relative centrifugal force) for 15 minutes.

Example 1

Comparison of Different Leukoreduction Filters

The efficacy of removal of leukocytes from whole blood spiked with 8E5 cells using three different leukoreduction filters (a Macopharmal filter, containing five layers, a Macopharma2 filter, containing six layers, and a Pall filter) was compared. Leukocyte removal by each filter was assessed using the three different methods described above: (i) white blood cell count by flow cytometric analysis; (ii) white blood cell quantification by RT and CD45 qPCR; and (iii) qPCR for HIV-1 proviral DNA.

Figure 1:
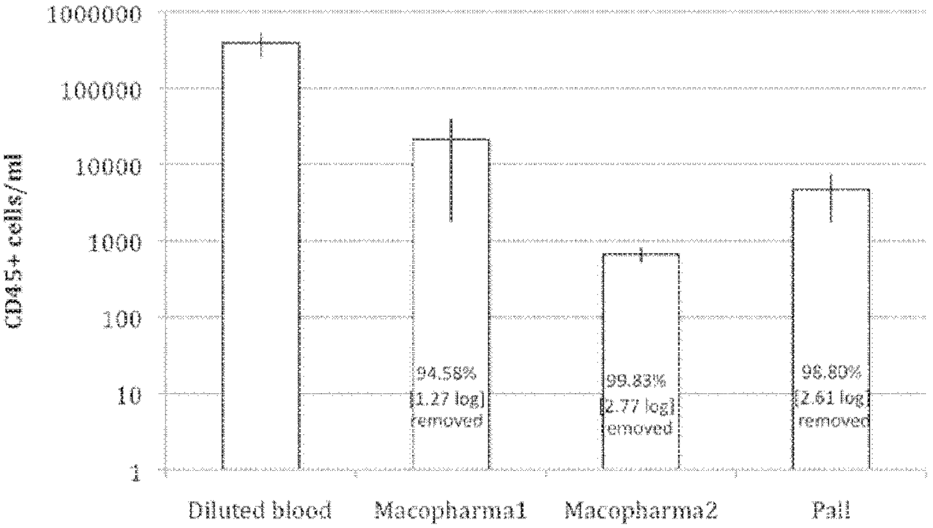
FIG. 1 shows leukocyte removal by different filter compositions from whole blood samples spiked with 100,000 8E5 cells/ml, tested by RT and CD45 qPCR. Error bars represent the standard deviation.
Figure 2:
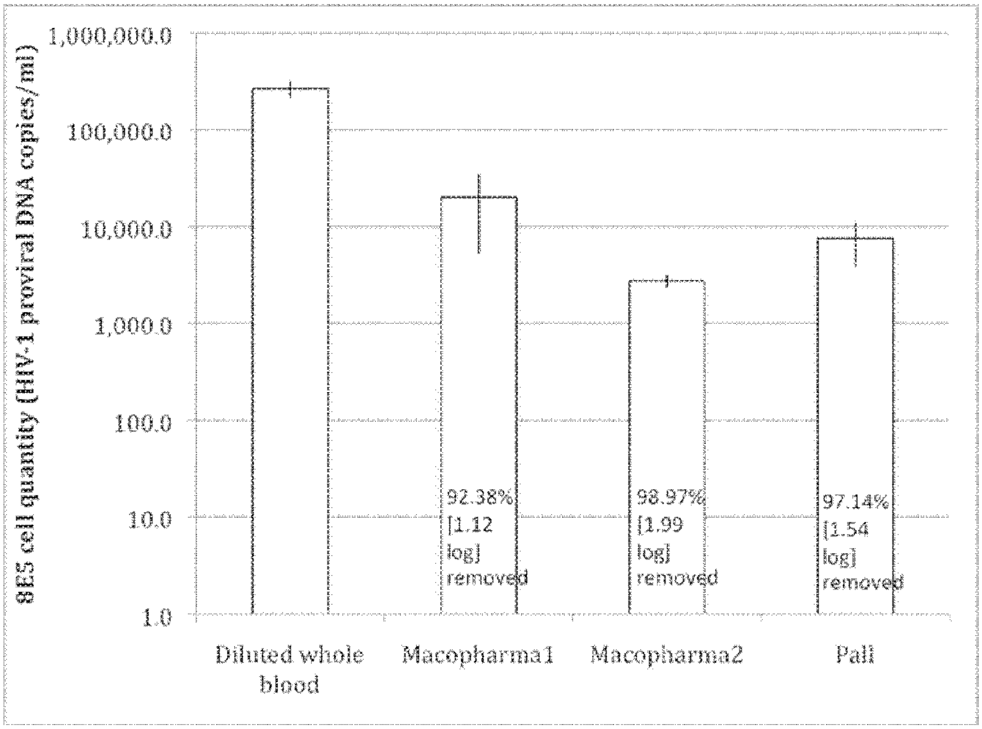
FIG. 2 shows 8E5 cell removal by different filter compositions from whole blood samples spiked with 100,000 8E5 cells/ml, tested by HIV-1 qPCR. Error bars represent the standard deviation.

The results as assessed by white blood cell (WBC) count by flow cytometry are shown in Table 1 below. The results as assessed by RT and CD45 qPCR are shown in FIG. 1, and the results as assessed by HIV-1 qPCR are shown in FIG. 2. Table 2 records the percentage leukocyte removal from the results shown in FIGS. 1 and 2.

TABLE 1

Leukocyte removal from whole blood as assessed by flow cytometry

| Sample | WBC count (cells/μl) | Log WBC Count | Log reduction compared to Diluted Whole Blood | % reduction compared to Diluted Whole Blood |
|---|---|---|---|---|
| Diluted whole blood | 723.00 | 2.86 | | |
| Macopharma1 filtered blood | 97.30 | 1.99 | 0.87 | 86.54 |
| Macopharma2 filtered blood | 0.80 | −0.10 | 2.95 | 99.89 |
| Pall filtered blood | 4.61 | 0.66 | 2.20 | 99.36 |
| Centrifuged plasma | 2.46 | 0.39 | 2.47 | 99.66 |

TABLE 2

| Percentage leukocyte removal from whole blood as assessed by RT and CD45 qPCR, and HIV-1 qPCR | | | | |
|---|---|---|---|---|
| Filter | Log reduction in leukocytes from diluted whole blood as assessed by RT and CD45 qPCR | % Leukocyte removal from diluted whole blood as assessed by RT and CD45 qPCR | Log reduction in leukocytes from diluted whole blood as assessed by HIV-1 qPCR | % Leukocyte removal from diluted whole blood as assessed by HIV-1 qPCR |
| Macopharma1 | 1.27 | 94.53 | 1.12 | 92.38 |
| Macopharma2 | 2.77 | 98.83 | 1.99 | 98.97 |
| Pall | 2.61 | 98.80 | 1.54 | 97.14 |

The results as assessed by flow cytometry show that 86.54% of leukocytes were removed using the Macopharmal filter, 99.89% of leukocytes were removed using the Macopharma2 filter, and 99.66% of were removed using the Pall filter. The results as assessed by CD45 qPCR show that 94.53% of leukocytes were removed using the Macopharmal filter, 99.83% of leukocytes were removed using the Macopharma2 filter, and 98.80% of leukocytes were removed using the Pall filter. The results as assessed by HIV-1 qPCR show that 92.38% of leukocytes were removed using the Macopharmal filter, 98.97% of leukocytes were removed using the Macopharma2 filter, and 97.14% of leukocytes were removed using the Pall filter.

The highest level of leukocyte removal was achieved using the Macopharma2 filter material. The lowest level of leukocyte removal was achieved using the Macopharmal filter material, and the Pall filter performed at an intermediate level. The Macopharma2 filter was used for subsequent experiments.

Example 2

Optimisation of Filter Thickness

The effect of the number of layers of filter material used for leukoreduction was determined. The Macopharma2 filter material used in Example 1 contained six layers. Since leukoreduction filters rely primarily on depth filtration to deplete the cell content, it was expected that increasing the number of layers of filter material would improve the efficacy of leukoreduction.

Figure 3:
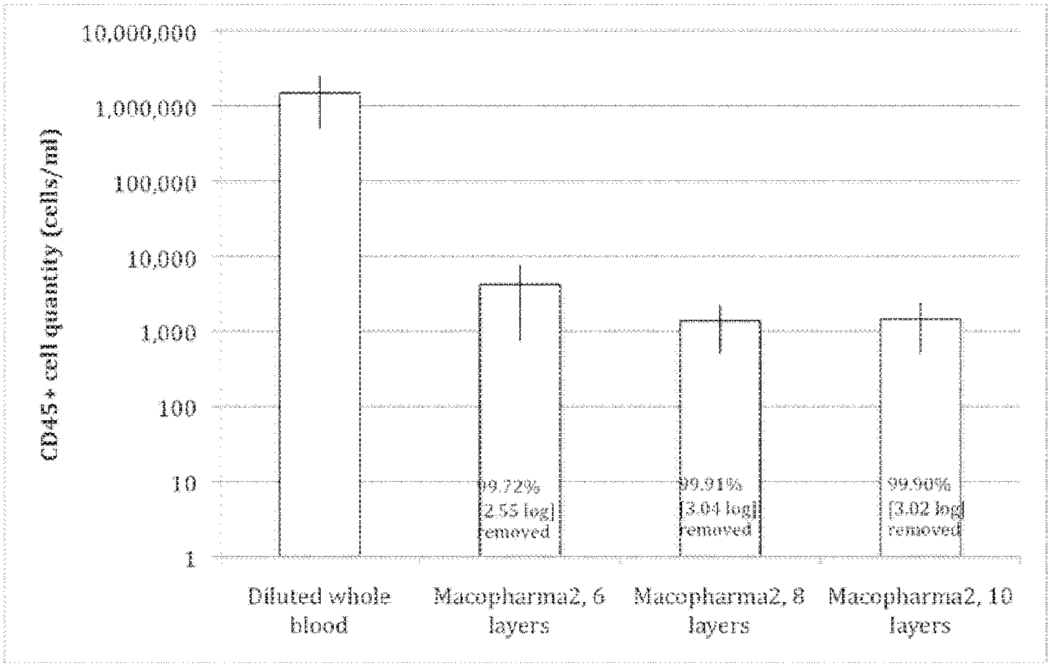
FIG. 3 shows leukocyte removal by filters of 6-10 layers from whole blood samples spiked with 100,000 8E5 cells/ml, tested by RT and CD45 qPCR. Error bars represent the standard deviation.

Whole blood samples spiked with 100,000 8E5 cells/ml were filtered using six, eight, or ten layers of the selected Macopharma filter. The efficacy of leukoreduction was determined by RT and CD45 qPCR, as described above. The results are shown in FIG. 3. Table 3 records the percentage leukocyte removal from the results shown in FIG. 3.

TABLE 3

| Percentage CD45+ cell removal from samples filtered using different numbers of layers of filter material | | |
|---|---|---|
| Number of layers | Log reduction in leukocytes from diluted whole blood as assessed by RT and CD45 qPCR | Percentage leukocyte removal from diluted whole blood as assessed by RT and CD45 qPCR |
| 6 | 2.55 | 99.72 |
| 8 | 3.04 | 99.91 |
| 10 | 3.02 | 99.90 |

The results show that a filter containing eight layers performs better than a filter with six layers. Greater than 3 log reduction (>99.9%) of white blood cells was obtained using eight layers of the Macopharma2 filter. However there was no significant difference in performance between filters of eight and ten layers.

The dead volume of each filter was determined by inserting the filter into a pre-weighed tube and centrifuging at 13,000 rpm for one minute. The tube was then re-weighed and the difference used to calculate the volume of liquid collected (given that the diluted blood has approximately the same density as water). The dead volume of the filter increases with the number of layers, as shown in Table 4.

TABLE 4

| Dead volume of different filter thicknesses, measured by liquid weight | |
|---|---|
| Number of layers | Average Dead volume (μl) |
| 6 | 39.2 |
| 8 | 50.8 |
| 10 | 77.2 |

Given the small starting volume of sample, a filter comprised of eight layers was selected because it achieves the desired reduction of ≥3 log white blood cells, with a dead volume of only ~50 μl.

Example 3

Optimisation of Sample Dilution

In view of the relatively small volumes of whole blood that can be collected without venipuncture, the effect of dilution of a small volume of a whole blood sample on the efficacy of leukoreduction was determined.

100 ul of whole blood (un-spiked) was diluted 1:2, 1:3, or 1:4 with phosphate buffered saline (PBS). The diluted samples were filtered using the selected Macopharma2 leukoreduction filter, and the level of white blood cell removal was assessed by RT and CD45 qPCR, as described above. No significant difference in the effectiveness of leukoreduction was observed using different sample dilutions.

The eight-layer Macopharma2 filter configuration was assessed for optimal sample dilution to pass sample through the filter, so as to achieve the optimal level of white blood cell removal when using an input of 100 μl of whole blood sample. A dilution of 100 μl of whole blood in 200 μl of phosphate buffered saline (PBS) (i.e. a dilution factor of 1:2) was found to be sufficient to allow blood to pass through the filter without diluting the sample excessively.

Example 4

Optimisation of Filtration Pressure

Samples of diluted whole blood were filtered through the selected Macopharma2 filter. The volume of air used was constant (1 ml), but the speed was varied. The level of white blood cell removal at the different pump speeds was assessed by RT and CD45 qPCR, as described above. The results are shown in Table 5.

TABLE 5

CD45+ cell removal from samples filtered under different pressures.

| Pump speed (µl/s) | CD45 PCR Quantification (cells/ml) | Log reduction in leukocytes from diluted whole blood | Percentage leukocyte reduction from diluted whole blood |
|---|---|---|---|
| Not filtered (diluted blood sample) | 1,657,652 | | |
| 25 | 1,129 | 3.17 | 99.93 |
| 50 | 1,198 | 3.14 | 99.93 |
| 100 | 2,082 | 2.90 | 99.87 |
| 200 | 3,150 | 2.72 | 99.81 |

The eight-layer Macopharma2 filter configuration was assessed for optimal pump speed to pass sample through the filter, so as to achieve the optimal level of white blood cell removal when using an input of 100 µl of whole blood sample. This was assessed by RT and CD45 qPCR as detailed above. A pump speed of 50 µl is was found to be optimal for 100 µl whole blood sample diluted in 200 µl PBS.

Example 5

Assessment of Leukodepletion of Spiked Whole Blood

Figure 4:
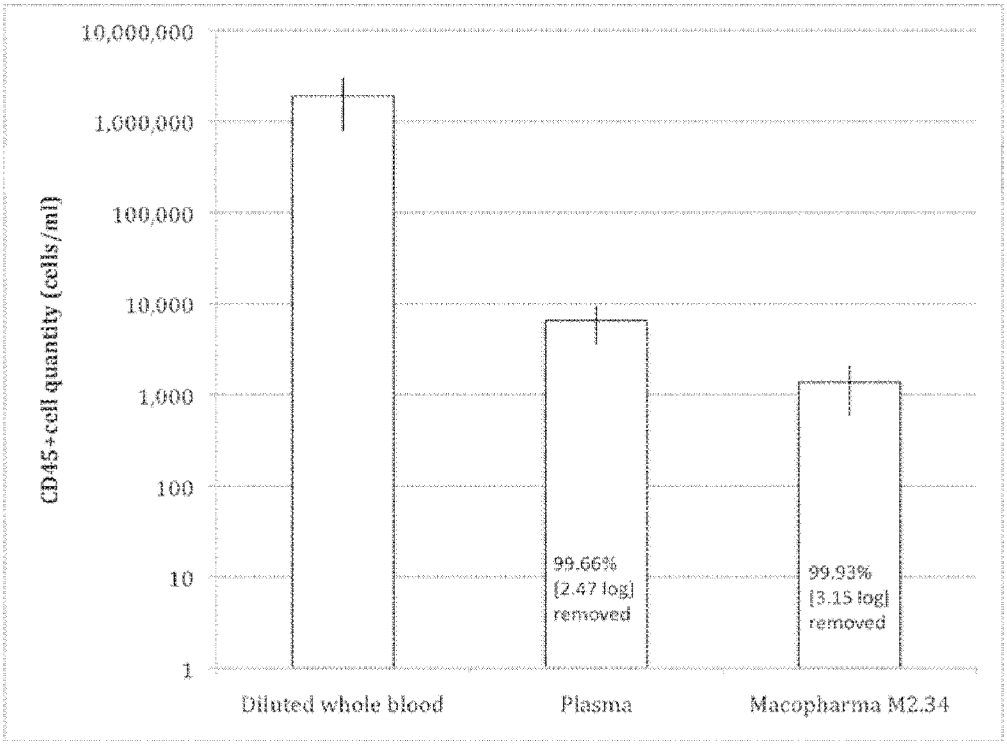
FIG. 4 shows leukocyte removal by centrifugation or filtration from whole blood samples spiked with 100,000 8E5 cells/ml, tested by RT and CD45 qPCR. Error bars represent the standard deviation.
Figure 5:
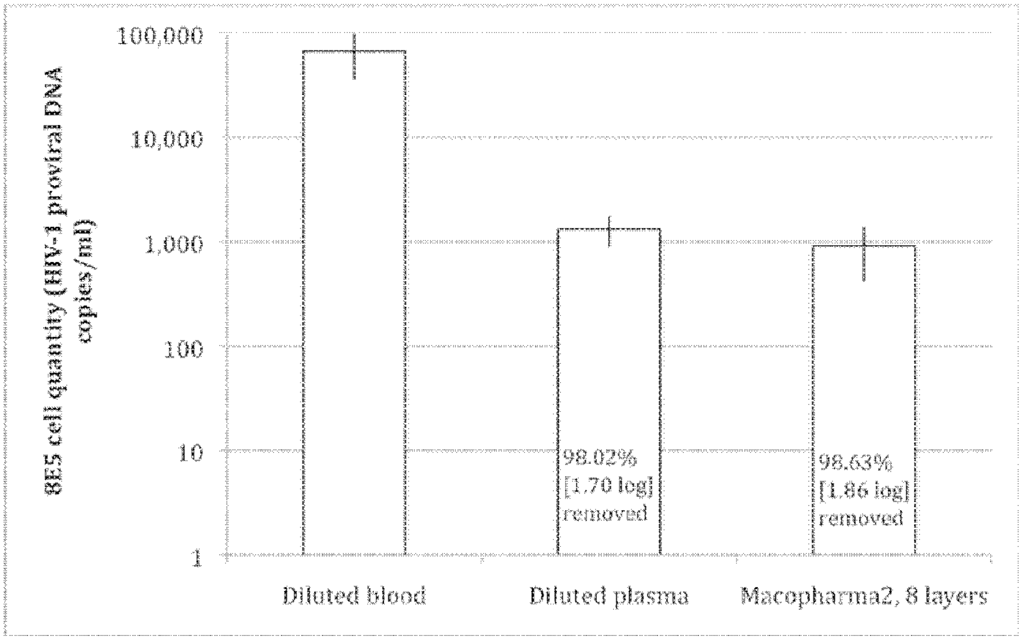
FIG. 5 shows 8E5 cell removal by centrifugation or filtration from whole blood samples spiked with 100,000 8E5 cells/ml, tested by HIV-1 PCR. Error bars represent the standard deviation.

The leukodepletion performance of the eight-layer Macopharma2 filter was assessed. Whole blood samples spiked with 100,000 8E5 cells/ml were filtered, and leukodepletion of the filtered samples was assessed using the three different methods described above: (i) white blood cell count by flow cytometric analysis; (ii) white blood cell quantification by RT and CD45 qPCR; and (iii) qPCR for HIV-1 proviral DNA. Leukodepletion of the filtered samples was compared to plasma samples (i.e. samples in which the cells have been removed from whole blood by centrifugation) since these are conventionally used for HIV viral load tests. The results obtained are shown in Table 6 below, and in FIGS. 4 and 5. Table 7 records the percentage leukocyte removal from the results shown in FIGS. 4 and 5.

TABLE 6

Leukoreduction by centrifugation or filtration from whole blood samples spiked with 100,000 8E5 cells/ml, assessed by flow cytometry.

| Sample | WBC count (cells/µl) | Average WBC count | Log Average WBC count | Log difference from whole blood | Percentage reduction from whole blood |
|---|---|---|---|---|---|
| Diluted whole blood | 1448.00<br>1573.00 | 1510.50 | 3.18 | | |
| Diluted plasma | 0.77<br>1.85 | 1.31 | 0.12 | 3.06 | 99.91 |
| Macopharma2 (8 layers) filtered blood | 1.08<br>0.15<br>0.26 | 0.50 | −0.30 | 3.48 | 99.97 |

TABLE 7

Percentage leukocyte removal from whole blood as assessed by RT and CD45 qPCR, and HIV-1 qPCR

| Sample | Log reduction of leukocytes from diluted whole blood as assessed by RT and CD45 qPCR | % Leukocyte removal from diluted whole blood as assessed by RT and CD45 qPCR | Log reduction of leukocytes from diluted whole blood as assessed by HIV-1 qPCR | % Leukocyte removal from diluted whole blood as assessed by HIV-1 qPCR |
|---|---|---|---|---|
| Plasma | 2.47 | 99.66 | 1.70 | 98.02 |
| Macopharma2 (8 layers) filtered blood | 3.15 | 99.93 | 1.86 | 98.63 |

As shown in Table 5, at a lower pump speed (and, therefore, at a lower pressure), there is a slightly higher level of removal of white blood cells. However, we have found that with decreasing pump speed there is an increase in filter dead volume. Thus, there may need to be a compromise between the efficacy of removal of white blood cells and the volume of sample lost to the filter.

The results as assessed by flow cytometry, and by RT and CD45 qPCR, show that filtration using eight layers of the selected Macopharma2 filter achieved greater than 3 log leukoreduction. By all methods of assessment, filtration of the whole blood sample achieved a greater level of leukoreduction than centrifugation.

Example 6

Assessment of Retention of HIV Particles by Leukoreduction Filter

This example describes an assessment of the degree to which HIV particles are retained by a leukoreduction filter when spiked whole blood samples are passed through the filter.

Figure 6:
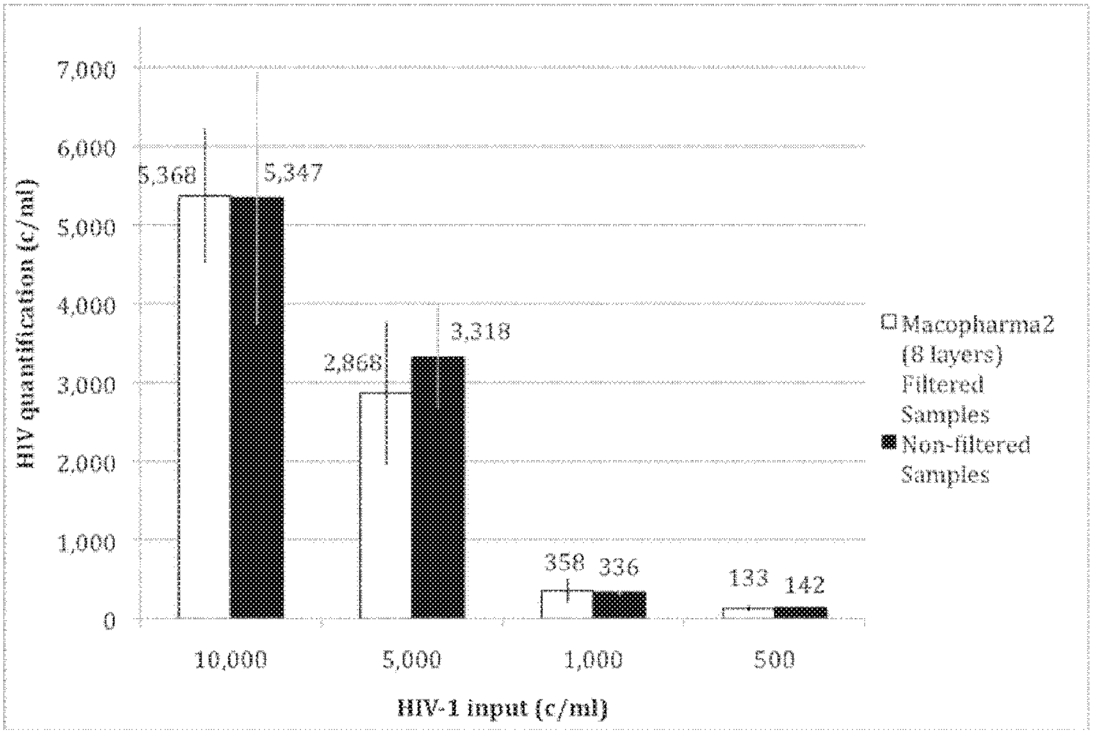
FIG. 6 shows free HIV-1 particle detection in filtered or unfiltered spiked whole blood samples at a range of input concentrations, tested by HIV-1 RT-qPCR. Error bars represent the standard deviation.

It is important that the filter does not retain any of the free HIV particles in circulation so that the viral load of the sample is not underestimated. To determine the level of retention of viral particles by the Macopharma2 filter, blood was spiked with various concentrations of culture supernatant of HIV-1 LAI (subtype B). The amount of HIV in the diluted blood samples before and after filtration was assessed by HIV-1 RT-qPCR. The results are shown in FIG. 6. Table 8 records the HIV concentration in copies/ml from the results shown in FIG. 6.

TABLE 8

Amount of HIV particles in blood samples before and after filtration

| HIV-1 input (c/ml) | HIV (c/ml) in Macopharma2 (8 layers) filtered blood | HIV (c/ml) in non-filtered blood |
|---|---|---|
| 10,000 | 5,368 | 5,347 |
| 5,000 | 2,868 | 3,318 |
| 1,000 | 358 | 336 |
| 500 | 133 | 142 |

The results show that there is no significant retention of HIV particles on the filter.

Example 7

Viral Load Testing of Spiked Blood Samples for Use in Resource-Limited Settings

In resource-limited settings, it is necessary to determine whether HIV viral load is below or above 1000 copies/ml. This Example describes a method for determining whether the HIV viral load of a sample is above or below 1000 copies/ml.

Blood samples were spiked with different concentrations of the World Health Organisation (WHO) 3rd International Standard for HIV-1 RNA (subtype B) (National Institute for Biological Standards and Control, NIBSC). The NIBSC viral stock is quantified in International Units (IU). There are approximately 1.7 copies of HIV per 1 IU.

100 µl whole blood samples were diluted in 200 µl phosphate buffered saline (PBS), and filtered through eight layers of the Macopharma2 filter material at a pump speed of 50 µl air per second.

Viral RNA was extracted, amplified by isothermal nucleic acid amplification, and the amplification products were detected by rapid visual detection with a dipstick, using a simple amplification-based assay (SAMBA) method similar to the method described in Lee et al., Journal of Infectious Diseases 2010; 201(S1):S65-S71.

Figure 7:
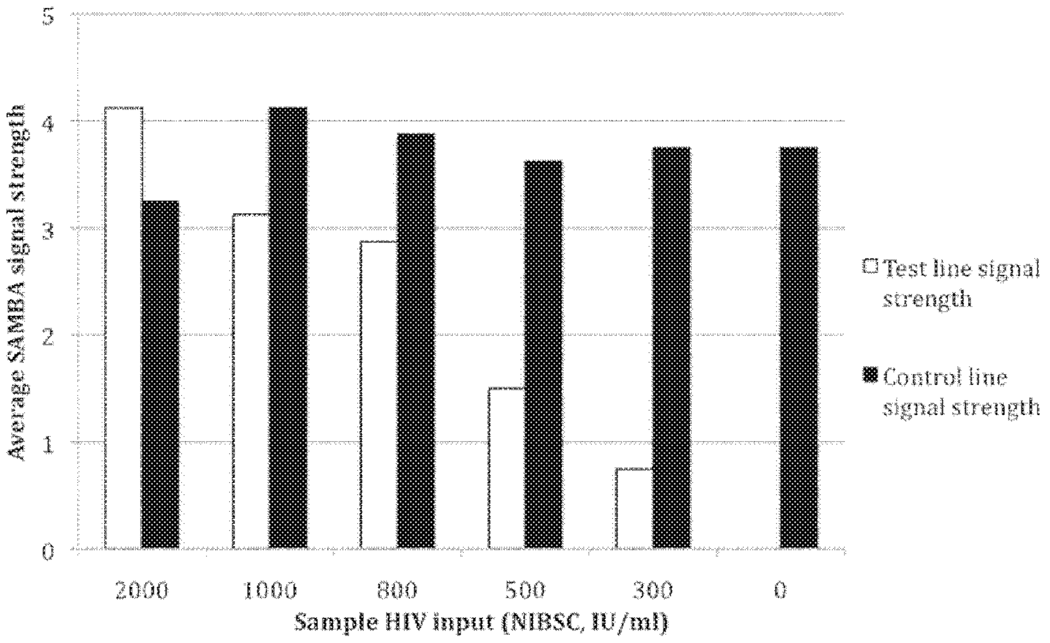
FIG. 7 shows average signal strengths of test and control lines on test strips at a range of input HIV concentrations.

The results are shown in FIGS. 7 and 8. The results shown in FIG. 7 demonstrate that a good average signal strength was obtained for test samples for which the HIV input was 800 or 1000 IU/ml. The results shown in FIG. 8 demonstrate that a positive test signal was obtained for ~75% of the samples for which the HIV input was 800 or 1000 IU/ml. It is concluded that the viral load test procedure described in this Example provides reliable results for determining whether or not a test sample has at least 1000 copies/ml HIV viral RNA, the cut-off for virologic failure in resource-limited settings.

Example 8

Viral Load Testing of Spiked Blood Samples for Use in Resource-Limited Settings

Blood samples were spiked with plasma samples from four patients collected in Namibia (HIV-1 subtype C) (each of which has a very high viral load; >30,000 copies/ml), and diluted in five doubling dilutions, with final viral load ranging between 120 and 6100 copies/ml.

120 µl whole blood samples were diluted in 240 µl phosphate buffered saline (PBS), and filtered through eight layers of the Macopharma2 filter material at a pump speed of 50 µl air per second.

Viral RNA was extracted, amplified by isothermal nucleic acid amplification, and the amplification products were detected by rapid visual detection with a dipstick, using a SAMBA method similar to the method described in Lee et al., Journal of Infectious Diseases 2010; 201(S1):S65-S71.

The results are shown in FIG. 9, and demonstrate that within the acceptable range given for viral load tests (3±0.3 $\log_{10}$ copies/ml) the procedure is 98.75% accurate.

Example 9

Viral Load Testing of Clinical Samples 207 whole blood samples from infected individuals, most of whom were undergoing treatment, were leukodepleted by filtration through a leukodepletion filter. Viral RNA was extracted, amplified by isothermal nucleic acid amplification, and the amplification products were detected by rapid visual detection with a dipstick, using a SAMBA method similar to the method described in Lee et al., Journal of Infectious Diseases 2010; 201(S1):S65-S71. The assay was designed to monitor HIV viral load with a cut-off of 1,000 copies/ml.

In parallel, the Roche COBAS AmpliPrep/COBAS TaqMan HIV-1 test was used to quantify the HIV viral copy in plasma, obtained by centrifugation at 2,200 g for 5 minutes. Testing by the SAMBA and Roche tests was completed on the same day for each patient sample. Plasma samples were stored frozen at −80° C. for discordant analysis using the Abbott RealTime HIV-1 test. Discordant samples for which there was insufficient sample to complete repeat testing were removed from the final analysis.

Table 9 below shows the distribution of the 198 samples remaining for the final analysis. Given that quantitation by the Roche COBAS AmpliPrep/COBAS TaqMan HIV-1 test has an accuracy of ±0.3 log, the comparative data were stratified into 4 categories: undetectable (no HIV target present); between 500 and 2,000 copies (i.e. within the 3±0.3 log 10 accuracy of the Roche test); <500 and >2,000 copies/ml.

TABLE 9

Distribution of HIV viral load measurement by SAMBA test compared to Roche COBAS AmpliPrep/COBAS TaqMan test

| | | Viral load measurement by Roche CAP/CTM (copies/ml) | | | |
|---|---|---|---|---|---|
| | | undetectable | <500 | 500-2,000 | >2,000 |
| SAMBA (copies/ml) | >1,000 | 0 | 8 | 6 | 24 |
| | <1,000 | 114 | 43 | 3 | 0 |

Overall concordance: 96%

It can be seen in this patient population that the leukodepletion filter was effective in removing the CD4+ cells, since the overall concordance between the Roche test, using plasma, and the SAMBA test, using leukodepleted whole blood, was 96% (190/198).

The invention claimed is:

1. A kit for HIV viral load testing, which comprises:

a leukoreduction filter which depletes at least 99.9% leukocytes from a whole blood sample or a diluted whole blood sample, and leaves at least 50% of the red blood cells present in the whole blood sample or the diluted whole blood sample remaining in the whole blood sample or diluted whole blood sample after filtration, wherein the leukoreduction filter is a depth filter or a screen filter having an average dead volume of 39.2 μl to 77.2 μl;

a blood collector with up to 500 μl capacity for collecting a low volume whole blood sample;

a means for applying a pressure differential across the leukoreduction filter; and reagents required for reverse transcription of HIV viral RNA, and subsequent nucleic acid amplification of a product of the reverse transcription, wherein the reagents required for amplification comprise primers for specific amplification of HIV nucleic acid.

2. The kit according to claim 1, further comprising an isotonic solution for diluting a sample of whole blood prior to leukodepletion of the sample.

3. The kit according to claim 1, further comprising a lancet for obtaining a sample of whole blood from a subject by finger prick or heel prick.

4. The kit according to claim 1, further comprising a visually detectable label for labelling a product of the nucleic acid amplification and/or a chromatographic test strip for capturing and detecting a product of the nucleic acid amplification.

5. The kit according to claim 1, further comprising means for extracting nucleic acid from a sample of leukocyte depleted blood.

6. The kit according to claim 1, wherein the reagents required for reverse transcription of HIV viral RNA comprise a reverse transcriptase, and the reagents required for nucleic acid amplification of a product of the reverse transcription comprise the following enzyme activities: an RNA-dependent DNA polymerase, a DNA-dependent DNA polymerase, a DNA/RNA duplex-specific ribonuclease, and a DNA-dependent RNA polymerase.

7. A kit according to claim 1, wherein the reagents required for nucleic acid amplification of a product of the reverse transcription are reagents required for isothermal amplification of the product.

8. A method of testing HIV viral load, comprising:

i) filtering a sample of whole blood, or a diluted sample of whole blood, through a leukoreduction filter of the kit of claim 1 to provide a sample of leukocyte depleted blood;

ii) reverse transcribing HIV viral RNA of the sample of leukocyte depleted blood using reagents of the kit of claim 1;

iii) amplifying, by isothermal nucleic acid amplification, a product of the reverse transcribing of step (ii) using reagents of the kit of claim 1, wherein the reagents required for isothermal amplification comprise primers for specific amplification of HIV nucleic acid; and iv) detecting the product of the isothermal nucleic acid amplification;

wherein the method is carried out without preparing a plasma sample.

9. A method of testing HIV viral load, comprising:

i) filtering a sample of whole blood, or a diluted sample of whole blood through a leukoreduction filter of the kit of claim 1 to provide a sample of leukocyte depleted blood in which at least 99.9% of the leukocytes have been depleted from the sample;

ii) reverse transcribing HIV viral RNA of the sample of leukocyte depleted blood using reagents of the kit of claim 1;

iii) amplifying, by isothermal nucleic acid amplification, a product of the reverse transcribing of step (ii) using reagents of the kit of claim 1; and iv) detecting the product of the isothermal nucleic acid amplification;

wherein the method is carried out without preparing a plasma sample.

10. A kit for HIV viral load testing, which comprises:

a leukoreduction filter which depletes at least 99.9% of leukocytes from a whole blood sample or a diluted whole blood sample and leaves at least 50% of the red blood cells present in the whole blood sample or the diluted whole blood sample remaining in the whole blood sample or diluted whole blood sample after filtration, wherein the leukoreduction filter is a depth filter or a screen filter having an average dead volume of 39.2 μl to 77.2 μl;

a means for applying pressure across the leukoreduction filter;

reagents required for reverse transcription of HIV viral RNA, and subsequent nucleic acid amplification of a product of the reverse transcription; and a lancet for obtaining a low volume sample of whole blood from a subject by finger prick or heel prick.

11. A kit according to claim 10, wherein the reagents required for nucleic acid amplification of a product of the reverse transcription are reagents required for isothermal amplification of the product.

* * * * *